United States Patent
Bergfjord

(10) Patent No.: US 8,942,348 B2
(45) Date of Patent: Jan. 27, 2015

(54) METHODS AND APPARATUS FOR PROVIDING ACCESSORIES TO A PATIENT DURING RADIATION TREATMENT

(75) Inventor: Per Harald Bergfjord, East Grinstead (GB)

(73) Assignee: Elekta, Ltd., Stockholm (SE)

( * ) Notice: Subject to any disclaimer, the term of this patent is extended or adjusted under 35 U.S.C. 154(b) by 340 days.

(21) Appl. No.: 13/369,511

(22) Filed: Feb. 9, 2012

(65) Prior Publication Data

US 2013/0208866 A1  Aug. 15, 2013

(51) Int. Cl.
*A61N 5/10* (2006.01)
(52) U.S. Cl.
USPC .............................................. 378/65; 378/204
(58) Field of Classification Search
CPC ..... A61N 5/10; A61N 5/1001; A61N 5/1007; A61N 5/103; A61B 6/46
USPC .......................................... 378/65, 204, 210
See application file for complete search history.

(56) References Cited

U.S. PATENT DOCUMENTS

| | | | |
|---|---|---|---|
| 4,538,289 A * | 8/1985 | Scheibengraber | 378/20 |
| 7,014,361 B1 | 3/2006 | Ein-Gal | |
| 7,581,264 B2 | 9/2009 | Mangiardi | |
| 7,869,858 B2 | 1/2011 | Calderon et al. | |
| 8,536,547 B2 * | 9/2013 | Maurer et al. | 250/492.3 |
| 2011/0249088 A1 | 10/2011 | Hannibal et al. | |

* cited by examiner

*Primary Examiner* — Jurie Yun
(74) *Attorney, Agent, or Firm* — Finnegan, Henderson, Farabow, Garrett & Dunner LLP

(57) ABSTRACT

An apparatus is provided for performing radiation therapy on a patient. In certain embodiments, the apparatus includes a patient support surface, a gantry having a radiation source rotatable around the patient support surface, a supply arm extending through the central bore, a supply interface disposed on the supply arm, and a supply line connecting the supply interface to a supply source. The apparatus delivers radiation therapy accessories to the patient while minimally interfering with access to the patient by radiation therapy personnel.

13 Claims, 5 Drawing Sheets

METHODS AND APPARATUS FOR PROVIDING ACCESSORIES TO A PATIENT DURING RADIATION TREATMENT

TECHNICAL FIELD

This invention relates to methods and apparatus for administering radiation therapy and, in particular, to methods and apparatus for providing treatment accessories to a patient treatment area while a patient is undergoing radiation therapy.

BACKGROUND INFORMATION

Tumors and lesions are pathological anatomies characterized by abnormal growth of tissue resulting from a progressive, uncontrolled multiplication of cells, while serving no physiological function. Pathological anatomies can be treated with invasive procedures, such as surgery, but these procedures can be risky and/or harmful for the patient.

A non-invasive method to treat a pathological anatomy (e.g., tumor, lesion, vascular malformation, nerve disorder, etc.) is external beam radiation therapy. In one type of external beam radiation therapy, an external radiation source is used to direct a sequence of x-ray beams at a tumor site from multiple angles. As the angle of the radiation source changes, each beam passes through the tumor site, but travels through a different area of healthy tissue on its way to the tumor. Ideally, the cumulative radiation dose at the tumor is high and the radiation dose to healthy tissue is low.

When preparing a patient for radiation therapy, various attachments and accessories are often used to help position the patient, monitor the patient's condition, provide sustenance, and/or control the patient's breathing. Many of these accessories require a supply of electrical power, a water supply, and/or an air supply. Generally these items require tubing or cabling that leads across the floor to where the patient is positioned. Having numerous cables and/or tubes lying on the floor in the area of the radiotherapy device is not optimal, particularly when a physician must enter the treatment area to effect a patient adjustment. For example, the physician may trip over or become entangled with the cabling or tubing. The cabling or tubing may also be damaged or become disconnected when it is bumped or otherwise contacted by the physician. Exposed cabling and/or tubing for radiation therapy accessories therefore presents a hazard that may jeopardize the health of the patient and/or result in damage to the radiation therapy equipment.

Accordingly, there is a need for an apparatus for delivering treatment accessories to a patient undergoing radiation therapy. In particular, a need exists for an apparatus that delivers radiation therapy accessories to a patient while minimally interfering with the treatment beams as well as access to the patient treatment area by doctors or radiation therapy technicians.

SUMMARY OF THE INVENTION

The present invention provides methods and apparatus for delivering treatment accessories, such as air, water, and electricity, to an area or region of a patient undergoing radiation therapy. The methods and apparatus minimize the cabling or tubing in the treatment area, and do not affect the operation of the radiation therapy machine. In certain embodiments, the accessories are delivered to the patient area through a central bore in a rotating gantry of the treatment device. In such cases, a supply arm passes through the central bore to the patient area and may be retracted (either manually or automatically) back through the bore when not in use. In other embodiments, the accessories are delivered through cabling and/or tubing that follows a path under the floor and up through a couch support to where the patient is positioned. In either arrangement, by avoiding the placement of cabling or tubing above and along the floor, the cabling and/or tubing is less likely to be contacted by a doctor or technician, and the risk of associated harm to the patient is minimized.

In one aspect, the invention relates to an apparatus for administering radiotherapy to a patient. The apparatus includes a patient support surface, a gantry having a radiation source rotatable around the patient support surface, and a central bore. A supply arm extends through the central bore such that the gantry rotates about the supply arm without the supply arm interfering with such rotation. A supply interface is disposed on the supply arm, and a supply line connects the supply interface to a supply source such that a portion of the supply line is disposed within the supply arm.

In certain embodiments, the supply line and the supply interface are configured to provide a gas, a liquid, and/or electricity. In one embodiment, the supply line includes a gas tube, a liquid tube, and/or a power supply cable. The supply arm may be extendable and may be retracted and extended through the central bore. The supply interface may be disposed along the supply arm, but in certain implementations it is located proximate the patient support surface.

In certain embodiments, the supply arm remains fixed in position while the radiation source rotates around the patient support surface. In certain embodiments, the apparatus includes a bearing between the gantry and the supply arm. A pendulum weight may be attached to the supply arm such that the pendulum weight maintains the supply arm at a fixed angular position while the gantry rotates.

In another aspect, the invention relates to an apparatus for administering radiotherapy to a patient. The apparatus includes a couch having a patient support surface and a couch support, and a gantry including a radiation source rotatable around the patient support surface. The apparatus also includes a supply interface disposed proximate the patient support surface, and a supply line connecting the supply interface to a supply source, wherein a portion of the supply line is disposed within the couch support.

In certain embodiments, the supply line and the supply interface are configured to provide a gas, a liquid, and/or electricity to the patient. The supply line may include a gas tube, a liquid tube, and/or a power supply cable. In one embodiment, the couch support is disposed on a floor, and a portion of the supply line is disposed beneath the floor such that the supply line travels from beneath the couch support through the couch support. At least a portion of the supply line may be disposed within a supply line tube.

The foregoing and other objects, features and advantages of the present invention disclosed herein, as well as the invention itself, will be more fully understood from the following description of preferred embodiments and claims, when read together with the accompanying drawings. In the drawings, like reference characters generally refer to the same parts throughout the different views. The drawings are not necessarily to scale, emphasis instead generally being placed upon illustrating the principles of the invention.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

While the invention is particularly shown and described herein with reference to specific examples and specific embodiments, it should be understood by those skilled in the art that various changes in form and detail may be made therein without departing from the spirit and scope of the invention.

DETAILED DESCRIPTION

It is contemplated that devices, systems, methods, and processes of the claimed invention encompass variations and adaptations developed using information from the embodiments described herein. Adaptation and/or modification of the devices, systems, methods, and processes described herein may be performed by those of ordinary skill in the relevant art.

Throughout the description, where devices and systems are described as having, including, or comprising specific components, or where processes and methods are described as having, including, or comprising specific steps, it is contemplated that, additionally, there are devices and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

Patients undergoing radiation therapy or technicians administering radiation therapy may require access to various accessories that require pressurized air, electricity, and/or water, during treatment sessions. In certain embodiments, access to the various elements needed (e.g., air, electricity, and/or water) is provided without the use of exposed cabling and/or tubing in the treatment area, and without affecting the operation of the radiation therapy machine.

Figure 1:
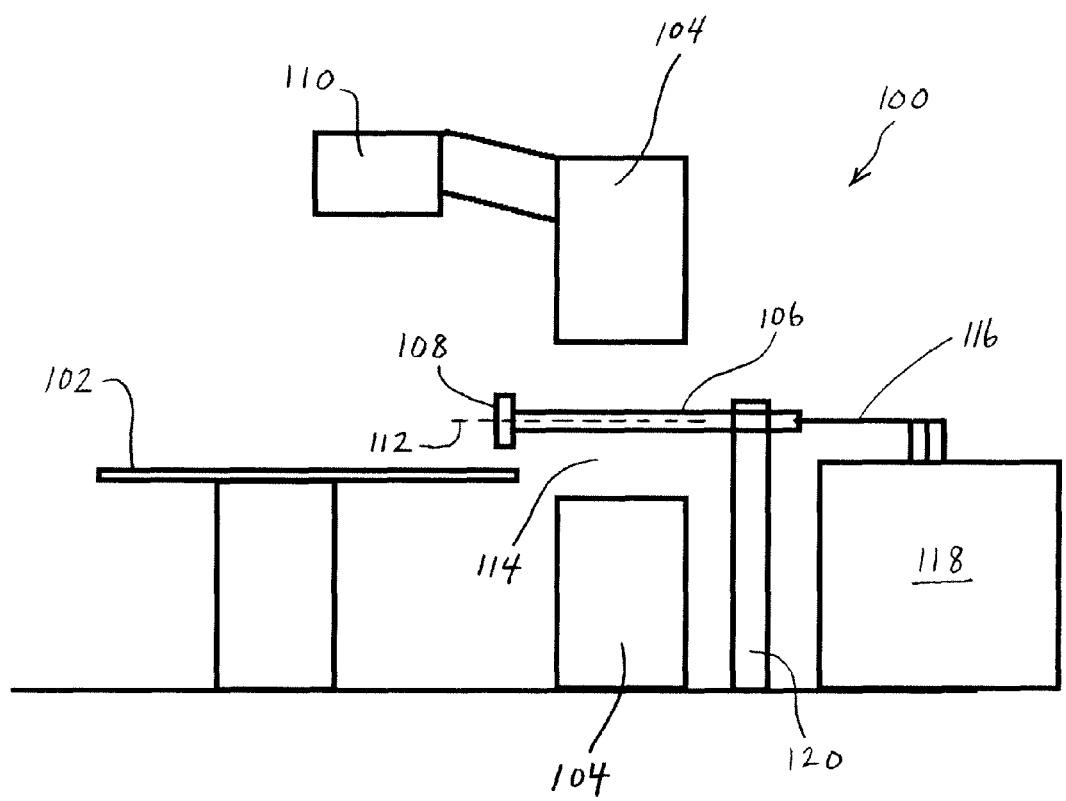
FIG. 1 is a schematic, cross-sectional, side view of an apparatus for administering radiation treatment in which a supply interface is positioned near a patient support surface, in accordance with one embodiment of the invention.

FIG. 1 is a schematic view of an apparatus 100 for administering radiation treatment, in accordance with one embodiment of the invention. The apparatus 100 includes a patient support surface 102, a gantry 104, a supply arm 106, and a supply interface 108. The gantry 104 includes a radiation source 110 rotatable around the patient support surface 102. An axis of rotation 112 for the gantry 104 and the radiation source 110 passes through a central bore 114 or opening within the gantry 104, which may be a wide-bore mounted gantry. During treatment, the supply arm 106 extends through the central bore 114 such that the gantry 104 is free to rotate about the axis of rotation 112 without interference from the supply arm 106. The supply interface 108 is disposed on or attached to an end of the supply arm 106. A supply line 116 connects the supply interface 108 to a supply source 118. At least a portion of the supply line 116 is disposed within or attached to the supply arm 106.

In certain embodiments, the supply line 116 and the supply interface 108 are configured to provide a supply or accessory to the patient area. The supply or accessory may be or include, for example, a means for operating a breath control device, such as the Active Breathing Coordinator™ (as supplied by Elekta Limited, UK), a patient fixation device such as a vacuum bag, or an imaging device, such as an ultrasound probe for in-treatment imaging. Such devices may require one or more of electricity for power and an air supply for the patient. In various embodiments, the supply or accessory may be or may utilize, for example, ambient air, positively or negatively pressurized air, water, and/or electricity. Accordingly, the supply line 116 may include one or more air tubes, water tubes, and/or electrical cables or wires. In one embodiment, at least a portion of the supply line 116 is encased within a tube or conduit.

The supply interface 108 may include, for example, a plurality of ports or sockets for connection of devices that require electrical power or the use of air and/or water. For example, the ports or sockets may be used to connect a tool, a suction tube, a marker/image projector, a marking device, an imaging device (e.g., a camera and/or video camera), a breathing tube, a breath control device, a sound recorder/projector, an air gun, a water spigot or spout, a lamp, and/or a patient fixation device. In certain embodiments, the ports or sockets are used to attach additional cabling or tubing to deliver the air, water, and/or electricity closer to the patient.

Figure 2:
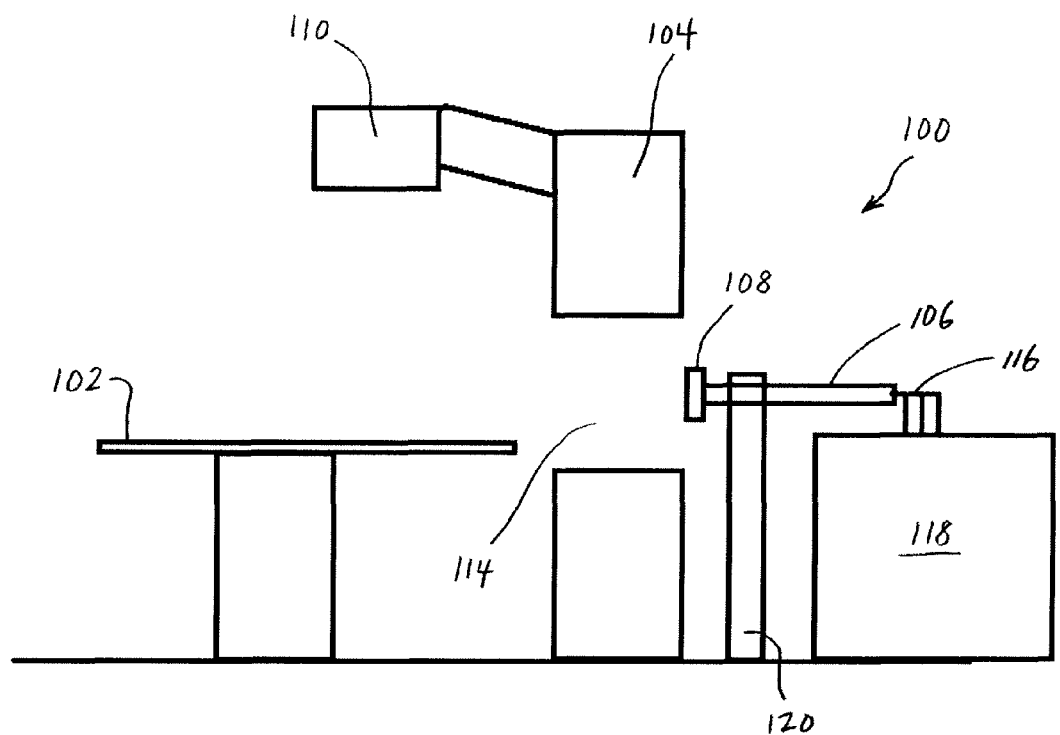
FIG. 2 is a schematic, cross-sectional, side view of an apparatus for administering radiation treatment in which a supply interface has been retracted through a central bore, in accordance with one embodiment of the invention.

In the depicted embodiment, the apparatus 100 also includes a support member 120 that supports and positions the supply arm 106 within the central bore 114. The support member 120 may include a motor or other mechanical components (e.g., bearings) for extending or retracting the supply arm 106 through the central bore 114. For example, as depicted in FIG. 1, the supply interface 108 on the end of the supply arm 106 may be positioned near or above the patient support surface 102 during treatment. Referring to FIG. 2, following treatment, the supply interface 108 and the supply arm 106 may be retracted (e.g., using the support member 120) through the central bore 114. In a retracted position, the supply interface 108 and supply arm 106 may be less likely to interfere with movement of the patient and/or radiation treatment personnel.

An advantage of the embodiments depicted in FIGS. 1 and 2 is that all of the cabling and/or tubing associated with the supply of accessories (e.g., air, water, and/or electricity etc.) may be contained within or secured to the supply arm 106, and is positioned away from the patient support surface 102, thereby minimizing the amount of cabling and/or tubing in the treatment area. The supply interface 108 may also be stowed away when not in use by retracting the supply arm 106 through the central bore 114, or, in some cases, removed from the supply arm and stored separately. Each of these features reduces the risk of contact between radiation therapy personnel and the accessory supplies, which in turn minimizes the risk of equipment damage and harm to the patient.

Figure 3:
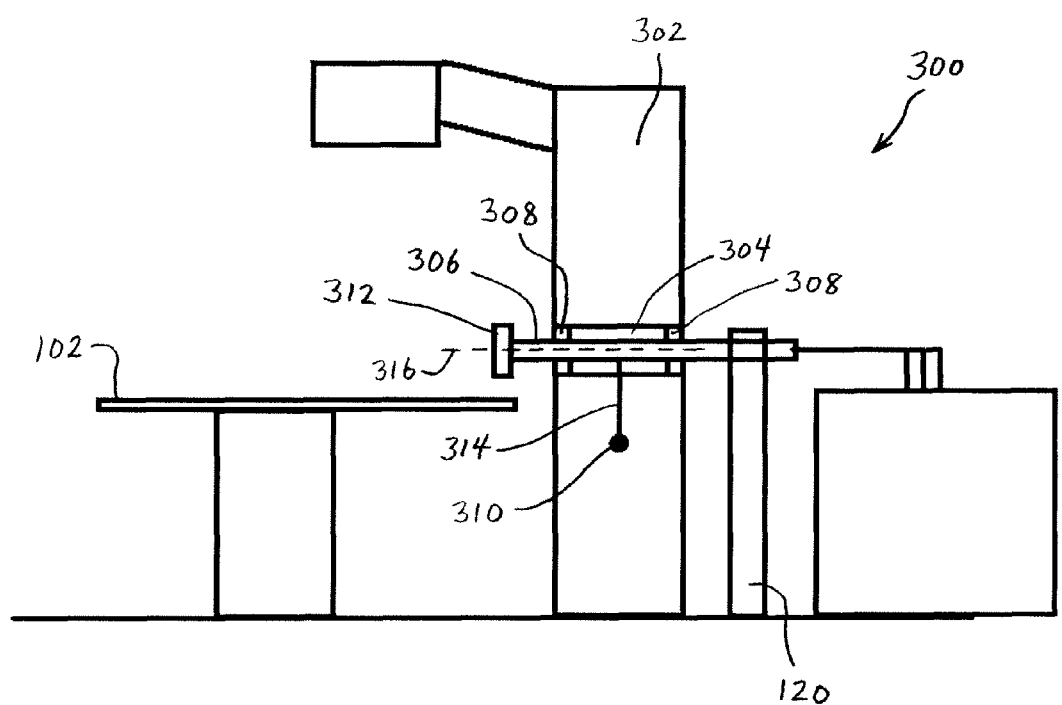
FIG. 3 is a schematic, cross-sectional, side view of an apparatus for administering radiation treatment that includes a pendulum weight, in accordance with certain embodiments of the invention.

FIG. 3 is a cross-sectional schematic side view of an apparatus 300 for administering radiation treatment, in accordance with certain embodiments of the invention. The apparatus 300 includes a gantry 302, a central bore 304, a supply arm 306, at least one bearing 308, a pendulum weight 310, and a supply interface 312. The at least one bearing 308 allows the gantry to rotate freely with respect to the supply arm 306. The pendulum weight 310 is attached to the supply arm 306 with a pendulum support 314. Gravity keeps the pendulum weight 310 suspended beneath the supply arm 306, which maintains the supply arm 306 and supply interface 312 at a desired angular position with respect to an axis of rotation 316 for the gantry 302. Alternatively, the angular position of the supply arm 306 may be fixed by attaching the supply arm to a component (e.g., the patient support surface 102, or the support member 120) that remains fixed wile the gantry 302 rotates. Accordingly, as the gantry 302 rotates about the supply arm 306, the supply arm 306 and supply interface 312 remain in a fixed angular orientation with respect to the axis of rotation 316. In certain embodiments, the gantry 302 is a drum-type gantry.

Figure 4:
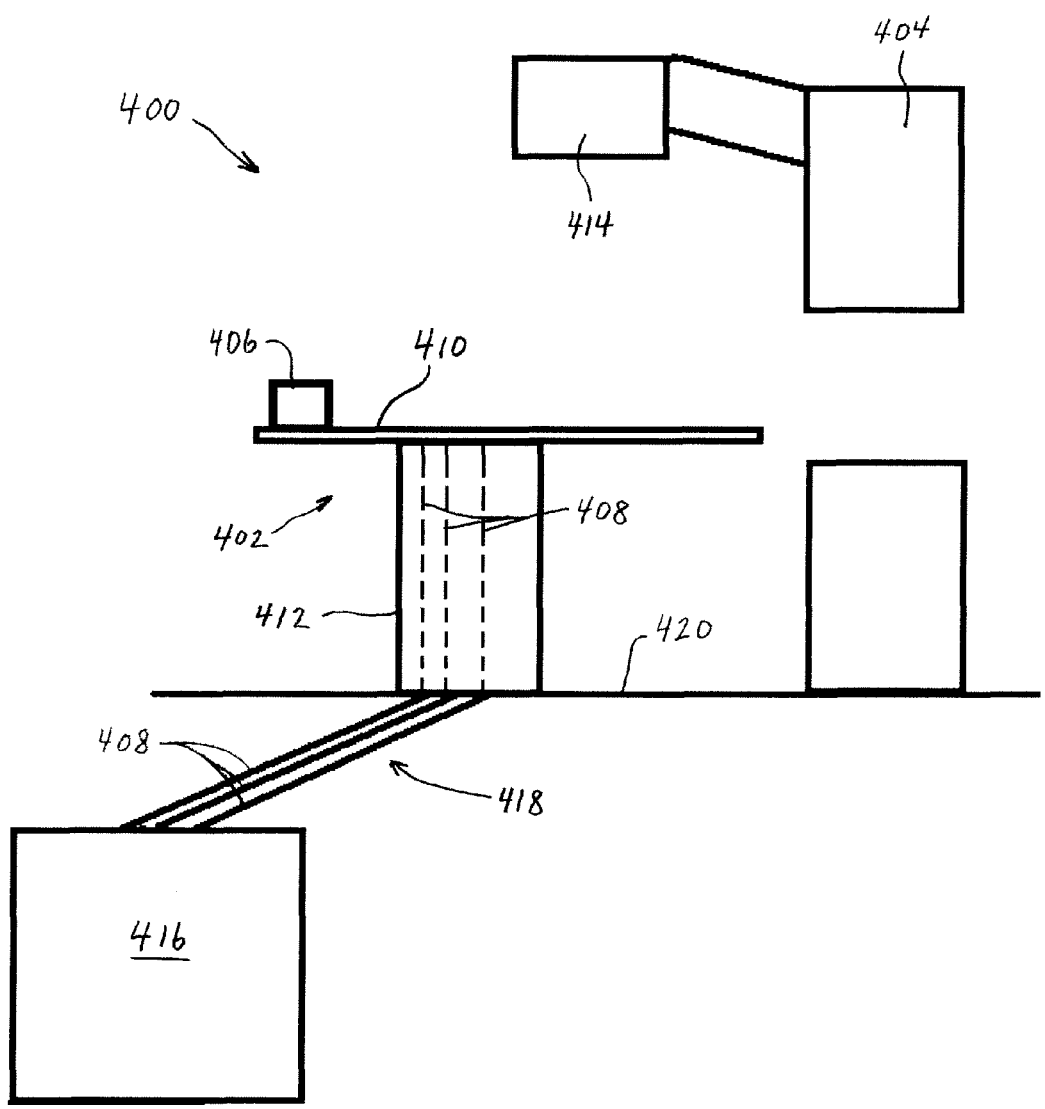
FIG. 4 is a schematic view of an apparatus for administering radiation treatment to a patient in which cabling or tubing is disposed along or under a floor, in accordance with certain embodiments of the invention.

FIG. 4 is a schematic view of an apparatus 400 for administering radiation treatment to a patient, in accordance with certain embodiments of the invention. As depicted, the apparatus 400 includes a couch 402, a gantry 404, a supply interface 406, and a supply line 408. The couch 402 includes a patient support surface 410 and a couch support 412. A radiation source 414 affixed to the gantry 404 rotates about the patient support surface 410. The supply interface 406 is attached to or disposed over or on the patient support surface 410. The supply line 408 connects the supply interface 406 to a supply source 416 (e.g., an air, water, and/or electricity source). At least a portion of the supply line 408 is attached to or disposed within the couch support 412.

In certain embodiments, the supply line 408 and the supply interface 406 are configured provide the patient with a supply or accessory. The supply or accessory may include or utilize, for example, air, water, electricity, and/or some other liquid (such as a saline solution) or gas (such as anesthetic) to be used before, during, or after treatment. Accordingly, the supply line 408 may include, for example, an air tube, a water tube, and/or an electrical cable or wire.

In the depicted embodiment, a floor segment 418 of the supply line 408 is disposed along a floor 420 between the supply source 416 and the couch support 412. In certain embodiments, the floor segment 418 is disposed beneath the surface of the floor 420. Alternatively, the floor segment 418 may placed on the surface of the floor 420 and covered with one or more mats or other floor surface coverings. In one embodiment, the floor segment 418 and/or another portion of the supply line 408 is encased within a tube or conduit. The supply line 408 follows a path within or along the couch support 412, from the floor 420 to the supply interface 406.

Similar to the embodiments described above with reference to FIGS. 1 and 2, this arrangement also provides a patient or technician with the needed supply interfaces, while significantly reducing the risk that the supply lines feeding the interfaces will interfere with treatment procedures.

Figure 5:
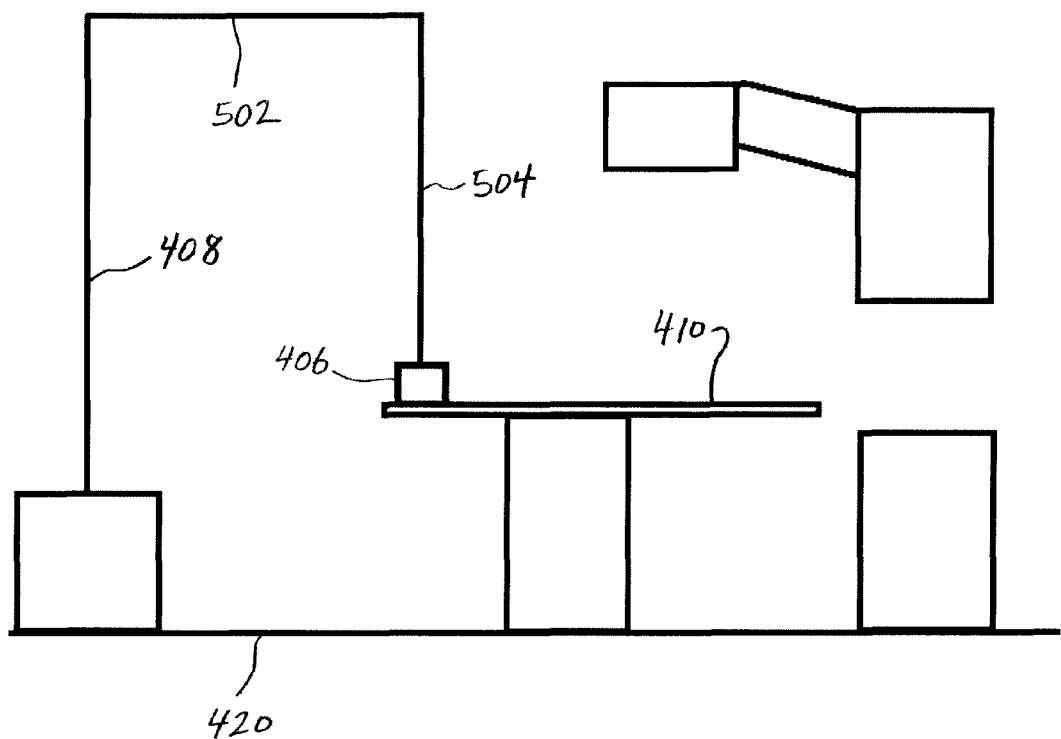
FIG. 5 is a schematic view of an apparatus for administering radiation treatment to a patient in which cabling or tubing is disposed along or through a ceiling, in accordance with certain embodiments of the invention.

Referring to FIG. 5, in certain embodiments, a portion of the supply line 408 is suspended from a ceiling or otherwise positioned high above the floor 420 so that it does not interfere with access to the patient treatment area by doctors or radiation therapy technicians. For example, the supply line 408 may follow a horizontal path 502 along or through the ceiling and a vertical path 504 down to the supply interface 406 near the patient support surface 410. In the case where the patient support may be raised, lowered tilted or rotated, the supply line can be made of a flexible material to allow it to follow the motion of the table without becoming disconnected.

While the invention has been particularly shown and described with reference to specific embodiments, it should be understood by those skilled in the area that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. An apparatus for administering radiotherapy, the apparatus comprising:
   a patient support surface;
   a gantry comprising a radiation source rotatable around the patient support surface, the gantry comprising a central bore;
   a supply arm extending through the central bore such that the gantry rotates about the supply arm without the supply arm interfering with such rotation;
   a supply interface disposed on the supply arm; and
   a supply line connecting the supply interface to a supply source, wherein at least a portion of the supply line is disposed within the supply arm.

2. The apparatus of claim 1, wherein the supply line and the supply interface are configured to provide at least one of a gas, a liquid, and electricity.

3. The apparatus of claim 1, wherein the supply line comprises at least one member selected from the group consisting of a gas tube, a liquid tube, and a power supply cable.

4. The apparatus of claim 1, wherein the supply arm is extendable and may be retracted through the central bore.

5. The apparatus of claim 1, wherein the supply interface is disposed proximate the patient support surface.

6. The apparatus of claim 1, wherein the supply arm is configured to remain fixed in position while the radiation source rotates around the patient support surface.

7. The apparatus of claim 6, further comprising a bearing between the gantry and the supply arm.

8. The apparatus of claim 6, further comprising a pendulum weight attached to the supply arm.

9. An apparatus for administering radiotherapy, the apparatus comprising:
   a couch comprising a patient support surface and a couch support;
   a gantry comprising a radiation source rotatable around the patient support surface;
   a supply interface disposed proximate to the patient support surface; and
   a supply line connecting the supply interface to a supply source, wherein at least a portion of the supply line is attached to an exterior surface of the couch support.

10. The apparatus of claim 9, wherein the supply line and the supply interface are configured to provide at least one of a gas, a liquid, and electricity.

11. The apparatus of claim 9, wherein the supply line comprises at least one member selected from the group consisting of a gas tube, a liquid tube, and a power supply cable.

12. The apparatus of claim 9, wherein the couch support is disposed on a floor, and wherein a portion of the supply line is disposed beneath the floor such that the supply line travels beneath the couch support.

13. The apparatus of claim 9, wherein at least a portion of the supply line is disposed within a supply line tube.

* * * * *